United States Patent
Ephstein

(10) Patent No.: US 8,178,498 B1
(45) Date of Patent: May 15, 2012

(54) MEDICAMENT AND METHOD OF TREATING AN ORGANISM WITH MEDICAMENTS

(76) Inventor: Oleg Iliich Ephstein, Moscow (RU)

(*) Notice: Subject to any disclaimer, the term of this patent is extended or adjusted under 35 U.S.C. 154(b) by 133 days.

(21) Appl. No.: 09/117,838

(22) PCT Filed: Feb. 10, 1997

(86) PCT No.: PCT/RU97/00026
§ 371 (c)(1),
(2), (4) Date: Apr. 12, 1998

(87) PCT Pub. No.: WO97/28776
PCT Pub. Date: Aug. 14, 1997

(30) Foreign Application Priority Data

| Feb. 12, 1996 | (RU) | 96102195 |
| Feb. 12, 1996 | (RU) | 96102209 |
| Apr. 24, 1996 | (RU) | 96107564 |

(51) Int. Cl.
*A61K 31/44* (2006.01)
*A61K 31/58* (2006.01)
*A61K 31/60* (2006.01)
*A61K 31/70* (2006.01)
*A61K 31/315* (2006.01)

(52) U.S. Cl. ......... 514/24; 514/159; 514/172; 514/304; 514/494

(58) Field of Classification Search ............ 424/455, 424/460, 484, 485, 486; 514/2, 4, 159, 172, 514/304, 494
See application file for complete search history.

(56) References Cited

U.S. PATENT DOCUMENTS

| 3,032,584 | A | * | 5/1962 | Stock et al. | 562/449 |
| 3,134,718 | A | * | 5/1964 | Nobile | 514/172 |
| 3,901,967 | A | * | 8/1975 | Cohen et al. | 514/304 |
| 4,292,324 | A | * | 9/1981 | Jonsson et al. | 514/494 |
| 4,839,341 | A | * | 6/1989 | Massey et al. | 514/4 |
| 4,963,367 | A | * | 10/1990 | Ecanow | 424/485 |
| 4,987,127 | A | * | 1/1991 | Sirany | 514/159 |
| 5,629,286 | A | | 5/1997 | Brewitt | |

FOREIGN PATENT DOCUMENTS

| DE | 2810344 C2 | | 11/1991 |
| EP | 0687 466 | * | 12/1995 |
| RU | 2007989 C1 | | 2/1994 |
| RU | 2033784 C1 | | 4/1995 |
| RU | 2035167 C1 | | 5/1995 |
| RU | 2042349 C1 | | 8/1995 |

OTHER PUBLICATIONS

International Search Report from International Application No. PCT/RU97/00026, filed Feb. 10, 1997, mailed on Apr. 8, 1997.
Grigoriev, M. Yu. et al., "K probleme ispolzovaniya potentsirovannykh organnykh preparatov," Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Vasiliev, Yu. V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.

* cited by examiner

*Primary Examiner* — Elli Peselev
(74) *Attorney, Agent, or Firm* — Gilman Pergament LLP

(57) ABSTRACT

A medicinal composition includes an active medicinal substance in therapeutic dose and a potentiated medicinal preparation produced from the substance by homeopathis methods.

25 Claims, No Drawings

MEDICAMENT AND METHOD OF TREATING AN ORGANISM WITH MEDICAMENTS

BACKGROUND OF THE INVENTION

This invention relates to medicine, namely, to medicinal preparations for use in therapy combining the methods of homeopathic and conventional therapy.

Contemporary pharmacotherapy extensively uses medicinal preparations produced chemically or derived from natural raw materials (of botanical, mineral or animal origin). These preparations exhibit therapeutic value and therefore can be applied in a certain range of therapeutic doses.

Also known are homeopathic medicines which contain therapeutic substances in minute, potentiated doses obtained by multiple successive dilution and shaking of the initial medicinal substance or of its trituration.

The latter group can be extended to preparations containing an indifferent material carrier (hereinafter referred to as 'carrier') (water, saline solution, alcohol, etc.) with bioenergetically transferred information on a bioactive substance obtained by homeopathic method (i.e. information on a homeopathic preparation); the field that the carrier posesses has a certain frequency spectrum (references: Patent of Germany 2810344, CL. A61H 39/00, 1984; Patent of Russian Federation 2033784, CL. A61H 39/00, 1995; Patent of Russian Federation 2042349, CL. A61J 3/00, 1995).

The principal disadvantages of the conventional medicines both in therapeutic and homeopathic doses are: discriminatory curative effect dependent on individual sensitivity and psychophysical state of the patient, and possible adverse undesirable after-effects.

Also known is a method of medicinal action on human organism by medical preparation exposed to external physical factor—gamma-radiation—which enhances activity of the medicine (Patent of Russian Federation 2035167, CL. A61K 35/64, 1995). Yet this approach has limited therapeutic applicability.

SUMMARY OF THE INVENTION

An object of the present invention is to create: a fundamentally new class of medicinal preparation (medicinal form) for more effective therapeutical action of the administered medicine; a method of medicinal influence on human organism, free of undesirable adverse after-effects, allergic and/or toxic reactions.

In accomplishing the foregoing objects, there is provided a medicinal preparation of a carrier with information on bioactive substance; according to the present invention, the preparation should constitute an active medicinal substance in therapeutic dose with bioenergetically transferred information thereto from potentiated medicinal preparation; the latter is produced by means of homeopathic methods and has initial chemical formula (composition) identical with that of the active medicinal substance.

DESCRIPTION PREFERRED EMBODIMENT OF THE INVENTION

The invention constitutes medicinal preparation comprising a carrier provided with information on a bioactive substance. According to the invention, the carrier comprises: (1) an active medicinal substance in therapeutic dose, (2) a potentiated medicinal preparation produced by methods of homeopathy and combined with (1) by admixing or incorporating thereto. The potentiated preparation has initial chemical formula (composition) identical to that of the active medicinal substance in therapeutic dose.

It is preferred that the active medicinal substance in therapeutic dose and potentiated medicinal preparation admixed thereto had similar (identical) medicinal form.

Also, in accomplishing the stated objects it is provided, in accordance with the invention, that in medicinal action on the organism the medicinal substance in therapeutic dose and potentiated medicinal preparation produced by homeopathic methods are administered simultaneously. The latter preparation has initial chemical formula (composition) identical to that of the former one. In doing this, the medicinal substance in therapeutic dose and the potentiated medicinal preparation may be administered as a single medicine combined thereof at the moment of production, or as separate medicinal forms administered simultaneously, but in either cases as medicines prepared separately.

Conceptually, the present invention claims a novel category (class) of medicinal preparations and/or medicinal forms that can be specified as "Bipathic", combining therapeutic values of medicinal substance in therapeutic dose and potentiated homeopathic preparation chemically homogeneous (in composition of the initial substance) but different in mechanism of action on the organism. This combination promotes biological activation and induces positive morphological and functional changes in form of "systemic adaptation" responsible for increased therapeutic efficiency of the active medicinal substance with reduced risk of patients' individual reactions and undesirable adverse after-effects.

Moreover, "bipathic" simultaneous administration of medicinal substance in therapeutic dose and potentiated preparation, according to the invention: (1) provides lower conventional doses of the substance, (2) prevents habituation due to enzyme "induction", (3) prevents overdosage owing to neutralization of negative energies and stimulation of certain organs and of the whole.

PREFERRED VARIANT OF REALIZATION

Medicinal action on the organism is effected by administration of the claimed "bipathic" medicinal preparation.

The medicinal preparation is produced, in accordance with the present invention, from medicinal substance (carrier) obtained chemically or derived from botanical, mineral or animal raw material with therapeutic properties; the preparation can be applied in any known dosage form (solid, liquid, soft, for injections) convenient for practical use in medicinal action on the organism.

EXAMPLE 1

Prior to transfer of bioenergetic information, 10 ml of 0.5% solution of atropine sulphate (medicine in therapeutic dose) as a carrier, and as a bioactive substance, potentiated preparation Atropini Sulfati C30 obtained by multiple successive dilution and shaking in accordance with homeopathic method, are placed in two separate containers mounted on current-conducting plates connected via a circuit of a known recorder of information signal. During bioenergetic information exchange, information about homeopathically potentiated initial active substance—atropine—is transferred to the carrier. The initial active substance has chemical formula identical to that of the carrier and possesses field with certain frequency spectrum. The obtained medicine is applied in ophthalmology as a mydriatic for diagnosis and treatment of inflammatory conditions; it is devoid of accommodation paralysis as an adverse effect.

EXAMPLE 2

0.01 g of potentiated homeopathic preparation Acidum Salicylicum is pressed into a pill containing 0.5 g of acetylsalicylic acid. The former is produced in accordance with homeopathic method by saturating a neutral substance, lactose, with solution of Acidum Salicylicum in C30 potency. By potentiating, the initial substance—acetylsalicylic acid—is bioenergetically transformed in accordance with homeopathic method into an information form, and the latter is directly transferred by pressing on the carrier, the carrier having a chemical formula identical to that of the initial substance. The "bipathic" medicine obtained so demonstrates effective analgesic, anti-inflammatory and antipyretic action with no adverse or allergic reactions. Its therapeutic effect in influenza is accelerated and augmented.

EXAMPLE 3

A total of 0.005 mg of potentiated prednisolone produced by homeopathic method in the 12th centile dilution (Cortex C12) is incorporated into a carrier—pill containing 1.0 ml of prednisolone—by impregnation with several capillaries. The obtained "bipathic" remedy influences actively carbohydrate and protein metabolism due to augmented anti-inflammatory, desensitizing and anti-allergic qualities of the initial therapeutic substance. When applied for endocrine disorders, it notably reduces severe metabolic disturbances, such as Cushing's syndrome. Positive results devoid of adverse complications can be obtained in cirrhotic liver.

EXAMPLE 4

A total of 1.0 ml of potentiated Insulinum C30 produced by homeopathic method through multiple dilution and shaking is admixed to liquid carrier containing 1.0 ml (40 U) of insulin for injections. In the mixture, the hormone demonstrates augmented and prolonged specific action to regulate carbohydrate metabolism, to stimulate assimilation of glucose in the tissues and to promote cellular glucose intake. The obtained "bipathic" remedy is administered in injections for diabetes mellitus and provides therapeutic efficiency at lower doses and reduced risk of adverse effects.

EXAMPLE 5

A total of 1.0 ml of potentiated remedy Zincum Metallicum produced by homeopathic method in soft form is incorporated into the carrier comprising 10 ml of zinc paste. The obtained "bipathic" remedy is applied in skin diseases. It demonstrates augmented antiseptic, disinfecting and astringent action devoid of skin irritation.

EXAMPLE 6

In therapy of neoplasms, 20 mg of sarcolysine is injected in 10 ml of saline solution synchronously ("bipathically") with a few (10-15) drops of oral potentiated Sarcolysinum in centile dilution C200. This method of therapeutical action provides lower toxicity of the active medicine and increased therapeutic efficiency.

INDUSTRIAL APPLICABILITY

To manufacture therapeutic preparation comprising a medicine in therapeutic dose as the carrier with bioenergetically transferred information on potentiated preparation produced by means of homeopathic methods and having initial chemical formula (composition) identical with that of the carrier, one can use known device for recording and transfer of information signal (refer to foregoing Patents: Patent of Germany 2810344; Patent of Russian Federation 2033784; Patent of Russian Federation 2042349).

In doing so the potentiated preparation is (1) produced from the initial substance by multiple successive dilution and shaking or trituration thereof with lactose in accordance with known homeopathic method and in any conventional dosage form (for example, refer to
[Гомеопатическиелекарственные средства. Руководствопоопиоанию иизготовлению. ДокторВильмарШвабе <<Руководствопоизгоговлению гомео патическихлекарств>> 1950 г. . Пер с немецкого. Под редакцией В. И. Рыбака. Москва, 1967.]) and (2) incorporated into carrier—the medicinal substance in therapeutic dose. The incorporation is performed synchronously with manufacturing of the carrier, for example: by pressing the pellets of lactose impregnated with solution of potentiated substance into the pills of active medicinal substance; by impregnation of the pills of active medicinal substance with dilution of potentiated substance; by mixing the noted components in the same (liquid or soft) dosage form. These procedures are technically accessible even for industrial application in a pharmacy.

What is claimed is:

1. A method of making a bipathic medication, comprising the steps of:
   providing an active medicinal substance in a therapeutic dose;
   providing a homeopathic dilution of said active medicinal substance; and
   admixing or incorporating said therapeutic dose and said homeopathic dilution with one another thus producing said bipathic medication.

2. The method of claim 1, wherein said admixing or incorporating step comprises impregnating said therapeutic dose with said homeopathic dilution.

3. The method of claim 2, wherein said bipathic medication is in the form of a liquid.

4. The method of claim 1, wherein said bipathic medication is in the form of a paste.

5. A bipathic medication comprising a pharmaceutically active combination of
   i) a therapeutic dose of an active medicinal substance; and
   ii) a homeophatic dilution of said active medicinal substance; said active medicinal substance and said homeophatic dilution being admixed or incorporated with one another;
   wherein said pharmaceutically-active combination possesses enhanced therapeutic properties in comparison with said active medicinal substance alone, said enhanced therapeutic properties being enhanced therapeutic effectiveness or reduced side effects.

6. The medication of claim 5, wherein said therapeutic dose of said active medicinal substance is impregnated with said homeopathic dilution.

7. The medication of claim 5, wherein said homeopathic dilution and said therapeutic dose of said active medicinal substance—are admixed with one another in a liquid state.

8. The medication of claim 5, wherein said homeopathic dilution and said therapeutic dose of said active medicinal substance—are admixed with one another as a paste.

9. The medication of claim 5, wherein said active medicinal substance is atropine sulfate.

10. The medication of claim 5, wherein said active medicinal substance is acetylsalicylic acid.

11. The medication of claim 5, wherein said active medicinal substance is prednizolon.

12. The medication of claim 5, wherein said active medicinal substance is insulin.

13. The medication of claim 5, wherein said active medicinal substance is a paste zinc.

14. The medication of claim 5, wherein said active medicinal substance is sarcolysin.

15. The medication of claim 9, wherein said homeopathic dilution is a C30 potency dilution.

16. The medication of claim 10, wherein said homeopathic dilution is a C30 potency dilution.

17. The medication of claim 11, wherein said therapeutic dose is 1.00 ml of prednizolon.

18. The medication of claim 17, wherein said homeopathic dilution has C12 potency.

19. The medication of claim 12, wherein said homeopathic dilution is a C30 potency dilution.

20. The medication of claim 13, which is in the form of a paste.

21. The medication of claim 14, which is in the form of aqueous solution of potassium chloride.

22. The medication of claim 14, wherein said homeopathic dilution has a C200 potency.

23. A method of treating a decease or condition in a mammal, said method comprising administering to said mammal a bipathic medication of claim 5.

24. The method of claim 23, wherein said therapeutic dose and said homeopathic dilution are admixed or incorporated with one another prior to administration.

25. The method of claim 23, wherein said mammal is human.

\* \* \* \* \*